United States Patent [19]

Hartmann et al.

[11] Patent Number: 5,560,859
[45] Date of Patent: Oct. 1, 1996

[54] POST FOAMING GEL SHAVING COMPOSITION

[75] Inventors: Barbara A. Hartmann, Clifton; Athanasios S. Ladas, Parsippany; Dino G. Muccia, Flanders, all of N.J.

[73] Assignee: Pfizer Inc., Del.

[21] Appl. No.: 457,180

[22] Filed: Jun. 1, 1995

Related U.S. Application Data

[63] Continuation of Ser. No. 963,242, Oct. 19, 1992, which is a continuation of Ser. No. 737,804, Jul. 29, 1991, which is a continuation of Ser. No. 387,241, Jul. 26, 1989.

[51] Int. Cl.$^6$ .............................. C11D 17/00; C11D 9/22; C11D 15/04; C11D 9/30
[52] U.S. Cl. .................. 510/135; 510/120; 510/137; 510/129; 424/47; 424/73; 8/405
[58] Field of Search .................... 252/90, 92, 117, 252/132, 174.13, 108

[56] References Cited

U.S. PATENT DOCUMENTS

| | | | |
|---|---|---|---|
| 3,541,581 | 11/1990 | Monson | 252/90 |
| 3,553,138 | 1/1971 | Mace | 252/90 |
| 3,574,118 | 4/1971 | Baker | 252/90 |
| 3,758,411 | 9/1973 | Healy | 252/90 |
| 3,811,349 | 5/1974 | Jennings | 83/14 |
| 4,148,743 | 4/1979 | Schubert | 252/132 |
| 4,169,067 | 9/1979 | Joshl | 252/132 |
| 4,192,862 | 3/1980 | Pengilly | 424/87 |
| 4,381,293 | 4/1983 | Michel | 424/14 |
| 4,528,111 | 7/1985 | Su | 252/107 |
| 4,708,813 | 11/1987 | Snyder | 252/90 |
| 4,772,427 | 9/1988 | Dawson et al. | 252/559 |

FOREIGN PATENT DOCUMENTS

| | | |
|---|---|---|
| 675664 | 12/1963 | Canada . |
| 1444334 | 7/1976 | United Kingdom . |

*Primary Examiner*—Anthony McFarlane
*Assistant Examiner*—Patricia L. Hailey
*Attorney, Agent, or Firm*—Peter C. Richardson; Paul H. Ginsburg; Grover F. Fuller, Jr.

[57] ABSTRACT

A post-foaming gel shaving composition is disclosed which contains from about 40 to about 90 percent by weight water; from about 4 to about 25 percent by weight water-soluble soap; from about 0.5 to about 12 percent by weight aliphatic liquid post-foaming agent selected from the group consisting of saturated aliphatic hydrocarbons; from about 0.01 to about 5 percent by weight of at least one water-soluble gelling agent forming in said composition a gel having a yield value sufficiently high to restrain said composition from foaming for at least about 60 seconds; and from about 0.1 to about 2 percent by weight of a poly(ethylene oxide) having an average molecular weight of at least $2\times10^5$.

12 Claims, No Drawings

POST FOAMING GEL SHAVING COMPOSITION

This is a continuation of application Ser. No. 07/963,242, filed on Oct. 19, 1992, which, in turn, is a continuation of application Ser. No. 07/737,804, filed on Jul. 29, 1991, which, in turn, is a continuation of application Ser. No. 07/387,241, filed on Jul. 26, 1989.

BACKGROUND OF THE INVENTION

The present invention relates to a post-foaming gel shaving composition.

U.S. Pat. No. 3,541,581 and British Patent Specification 1444334 refer to post-foaming gel shaving compositions.

The composition of the present invention is a lather-producing composition that can be discharged from an aerosol container as a clear, stable gel substantially free from foaming, which after application to the skin and beard produces a self-generating foam. The composition of the present invention provides a thicker and more stable lather, over the prior art compositions, improved wetting of the skin and beard, more of a lubricious feel to the skin, and improved gel adhesion to the skin. The composition is stable for long storage periods at ambient temperatures.

SUMMARY OF THE INVENTION

The present invention relates to a cleansing or cosmetic composition in the form of a stable, post-foaming gel consisting essentially of from about 40 to about 90 percent by weight water; from about 4 to about 25 percent by weight water-soluble soap; from about 0.5 to about 12 percent by weight aliphatic liquid post-foaming agent selected from the group consisting of saturated aliphatic hydrocarbons; from about 0.01 to about 5 percent by weight of at least one water-soluble gelling agent forming in said composition a gel having a yield value sufficiently high to restrain said composition from foaming for at least about 60 seconds; and from about 0.1 to about 2 percent by weight of a water-soluble poly(ethylene oxide) having an average molecular weight of at least $2 \times 10^5$.

In a preferred embodiment of the present invention, the amount of water in the composition is about 50 to about 80% by weight.

In another preferred embodiment of the invention, the poly(ethylene oxide) has a molecular weight of about $2 \times 10^5$ to about $6 \times 10^6$, more preferably, about $3 \times 10^5$ to about $6 \times 10^5$. The most preferred molecular weight is about $4 \times 10^5$.

In another preferred embodiment of the present invention, the composition contains about 0.3 to about 0.8 percent by weight poly(ethylene oxide).

In another preferred embodiment of the present invention, the poly(ethylene oxide) has a molecular weight of about $3 \times 10^5$ to about $6 \times 10^5$ and the composition contains about 0.3 to about 0.8 percent by weight poly(ethylene oxide).

In another preferred embodiment of the present invention, the composition contains about 1 to about 4% by weight of post-foaming agent.

In another preferred embodiment of the present invention, the post-foaming agent is a liquid that has a vapor pressure about atmospheric (14.7 psia) at a temperature of about 40° C.

In another preferred embodiment, the soap is present at from about 8 to about 15% by weight.

In another preferred embodiment of the invention, the gelling agent is hydroxypropylcellulose. When hydroxypropylcellulose is the gelling agent, it is preferably present at a concentration of about 0.025 to about 1.5% by weight.

A preferred formulation of the present invention comprises about 70 to about 80% by weight water, about 8 to about 10% of a $C_{12}$ to $C_{18}$ fatty acid (e.g., palmitic acid), about 5 to about 6% by weight triethanolamine, about 1 to about 2% by weight propylene glycol isostearate, about 1 to about 2% by weight of an aqueous solution of sorbitol that is about 60 to about 80 percent by weight sorbitol, about 0.3% to about 0.8% by weight of poly(ethylene oxide) having a molecular weight of about $3 \times 10^5$ to about $6 \times 10^5$, 0 to about 1% by weight of fragrance, about 0.02 to about 0.03% by weight of hydroxypropylcellulose, and about 2 to about 3% by weight of a liquid hydrocarbon having a vapor pressure of about 14.7 psia at 40° C. The foregoing formulation may also contain an appropriate amount of a compatible dye.

The present invention also relates to a homogeneous composition comprising the post-foaming gel of the present invention with a propellant dispersed continuously throughout the gel.

The present invention also relates to an aerosol container comprising the post-foaming gel of the present invention together with a propellant.

The present invention also relates to a foam composition comprising a foamed gel of the present invention.

DETAILED DESCRIPTION OF THE INVENTION

The composition of the present invention is preferably a clear gel with propellant dispersed continuously throughout the gel.

As used herein, unless indicated otherwise, the term post-foaming gel means a gel which remains substantially free from foaming for at least about 60 seconds when discharged from a pressure tight container under static ambient conditions (about 20° C., at approximately one atmosphere of pressure under conditions substantially free from shearing tension).

The compositions of the present invention may also include emollients, humectants, surfactants, fragrances, flavors (e.g. menthol) and dyes.

A preferred emollient is propylene glycol isostearate (available as Emerest 2384 from Emery Chemical Company) which is an ester of propylene glycol and isostearic acid. Another suitable emollient is lanolin alcohol (available as Ceralan from Amerchol Corporation).

A preferred humectant is sorbitol, available as Liponic 70NC from Lipo Inc.

As used herein, the term non-crystallizing sorbitol solution refers to an aqueous polyol solution that contains at least about 45 percent by weight sorbitol, 0.2 percent reducing sugars, about 20 percent by weight of non-volatile components such as anhydrides of D-sorbitol, and at least about 29 percent by weight water. This solution does not crystallize at 0° C., while USP Sorbitol crystallizes at about 25° C. The preferred material is LIPONIC 70-NC (trademark) available from Lipo Chemicals, Inc. of Paterson, N.J. The latter material contains 29–30 percent by weight water, 45–55 percent by weight sorbitol, 0.2 percent reducing sugars, and about 20 percent by weight of non-volatile components such as anhydrides of D-sorbitol.

A sorbitol solution containing about 60 to about 70 percent by weight sorbitol, preferably about 64 to about 70 percent by weight sorbitol and the remainder water (said solution preferably consisting essentially of sorbitol and water), may be substituted for the aforementioned non-crystallizing sorbitol solution in the formulations of the present invention. Other sweeteners that form viscous solutions, such as corn syrup or glucose, may also be substituted for the non-crystallizing sorbitol solution in the formulations of the present invention.

The soap ingredient of the present composition is a water-soluble salt of high purity fatty acids, made by reacting an alkali such as triethanolamine with higher ($C_{12}$ to $C_{18}$) fatty acids such as palmitic, stearic, myristic, lauric, oleic, coconut oil, soya oil, and mixtures thereof. The salts are formed by a neutralization of the fatty acids, and the amount of alkali required can be calculated from the average molecular weight of the fatty acid. Most of the fatty acids used are obtained from naturally occurring fats and oils. The preferred fatty acid is a high-purity saturated fatty acid with an approximate 90% by weight palmitic acid content. A specific preferred fatty acid is Hystrene 9016, available from the Humko Division of Witco Corporation. The typical carbon chain composition of Hystrene 9016 is 92% palmitic ($C_{16}$), 7% stearic ($C_{18}$), and 1% myristic ($C_{14}$) acid. The nature of the soap ingredient has an effect on the type of gel and lather produced. Mixtures of various soaps may be used to obtain the desired properties.

The post-foaming agent of the present composition is a liquid at room temperature and includes hydrocarbons having 3–6 carbon atoms, such as propane, butanes, pentanes, and hexanes. The preferred agent is a blend of isopentane (80.0% by weight minimum) n-pentane (3.5% by weight maximum), neo-pentane (1.0% by weight maximum), isobutane (12.5% by weight minimum), and butane/propane about 0.40% weight butane and about 0.16% by weight propane, more preferably 85% by weight isopentane and 15% by weight isobutane (0.56% by weight of the mixture maximum). Mixtures of hydrocarbons are desirable for providing the particular vapor pressure desired to control the rate of foam development. The higher the vapor pressure of the gel, the more rapidly the foam develops, and the vapor pressure of the gel is determined mostly by the post-foaming agent. The vapor pressure of the post-foaming agent must render the gel substantially free from foaming for at least 60 seconds when dispensed under static ambient conditions and should then volatilize to produce a foam. For instance, if a 85/15 isopropane/isobutane mixture at 70° F. (21° C.) is used, this mixture has a vapor pressure of 17.8 psia. The concentration and type of post-foaming agent used in the gel are determined by such factors as gel stability, foam profile, and post-foaming characteristics. The post-foaming agent should be dispersed homogeneously throughout the gel.

Suitable gelling agents for the use in the composition of the present invention are water-soluble resins derived from natural substances including cellulose, glucose, and sucrose. The preferred gelling agent, hydroxypropylcellulose (Klucel HF, Aqualon Co.), is a nonionic water-soluble propylene glycol ether of cellulose made by reacting alkali cellulose with propylene oxide at elevated temperatures and pressures. There are many viscosity grades of hydroxypropylcellulose available that are suitable for use in the compositions of the present invention, with the higher viscosity grade being preferred.

The poly(ethylene oxide) used in the compositions of the present invention acts as a gel stabilizer. A specific preferred poly(ethylene oxide) is PEG-14M (Polyox WSRN-3000, Union Carbide Corp.). This resin is a non-ionic water-soluble homopolymer that hydrogen-bonds strongly with water, and the resulting complex develops a high degree of stretch, thereby substantially restraining the post-foaming agent from volatilizing under static ambient conditions. Other poly(ethylene oxide) resins which may be used are Polyox WSRN-10(M.W. 100,000); Polyox WSRN-80(M.W. 200,000), Polyox WSRN-750(M.W. 300,000), Polyox WSRN-3333(M.W. 400,000), Polyox WSR-205(M.W. 600,000), Polyox WSRN-12K(M.W. 1,000,000), and Polyox WSRN-60K (M.W. 2,000,000). The resin may also affect the vapor pressure of the gel and post-foaming agent.

The poly(ethylene oxide) used in the compositions of the present invention helps prevent the gel from foaming for the required period of time. This polymer also contributes to product clarity, enhancement of foam quality, tolerance for entrapped air, improved adhesion to the skin, improved lubricity and improved stability.

In an aerosol container of the present invention, a liquified gas propellant may be dispersed as droplets throughout an emulsion comprising the components of the gel of the present invention. When the product is discharged, the propellant vaporizes into a gas that is trapped by the emulsion which forms a foam.

The emulsion comprising the components of the gel of the present invention is prepared by forming an aqueous soap intermediate from reacting an alkali with higher fatty acid as described above at 75°–80° C. Prior to forming the soap, an emollient and a cellulosic are added to the fatty acid and a humectant, dyes and surfactants may be added to the aqueous phase. A solution of the gelling aid is then prepared and added to the aqueous phase.

To prepare the solution of the gelling aid for the emulsion comprising the components of the gel of the present invention, the poly(ethylene oxide) resin, for example PEG-14M (Polyox WSRN-3000, Union Carbide Corp.), is incorporated into water using a suitable means of rapid agitation e.g. an eductor (flocculant disperser) which is used to keep the water soluble resin particles from sticking together. Various additives such as surfactants, fragrances or flavors and menthol may be added to the soap intermediate before cooling to 2°–8° C. with agitation.

A post-foaming agent (for example, an 85:15 blend of isopentane/isobutane propellant) is blended into the final mixture, avoiding air entrapment. Since isopentane and isobutane are incorporated into the gel, it is necessary to produce the final pressurized composition under cold conditions (2°–8° C.) in order to prevent pre-foaming of gel due to volatilization.

The final pressurized product is prepared by incorporating an 85:15 blend of isopentane/isobutane at approximately a 3.0% level into the gel concentrate. The gel concentrate/propellant blend is filled into an appropriate barrier pack (which includes collapsible metal tubes and aerosol dispensers). When using an aerosol dispenser, the post-foaming gel must be maintained separately from the propellant by means of a bag or a diaphragm inside the package. Both may be driven by a propellant. Care must be taken to keep propellant separate from the gel. The container is pressurized with approximately 10 grams of a hydrocarbon propellant (e.g. isobutane, A-31 propellant). The filled and pressurized can is then plugged. The pressure of the container should range from 45–55 psig at 70° F.

The stable post-foaming gel can be packaged in a variety of container systems. The "bag-in-can system" basically consists of a metal 3 piece can equipped with an inner plastic bag fastened to the dome that contains the gel/post-foaming agent mixture. The propellant is loaded through the bottom of the can which is perforated for a charging plug, and the propellant remains separate from the bag. The container is designed to use hydrocarbons, and other compressed gasses. The bag serves as a barrier to prevent the gel/post-foaming agent mixture from coming in contact with the propellant around the bag. The bag is made of polyethylene, Surlyn and nylon and has pleated side walls which enable the bag to collapse upward as the propellant force empties the container. The bag is capable of discharging very viscous materials. A major problem with this unit is gas permeation through the bag into the gel. Permeation occurs "when significant number of molecules pass through a barrier during a fixed time period." Larger molecules permeate more slowly than smaller ones. Entrapment of air in the gel when filling into the can can be minimized by use of a spin filler, which rotates the cans while gel is transferred into the bag.

The following Example illustrates the formulations of the present invention.

EXAMPLE

A formulation is prepared from the following ingredients as described below:

| Ingredients | % by wt. |
| --- | --- |
| Water | 77.95 |
| Palmitic Acid (Hystrene 9016) | 9.74 |
| Triethanolamine | 5.65 |
| Propylene Glycol Isostearate (Emerest 2384) | 1.70 |
| Sorbitol (Liponic 70 NC) | 1.46 |
| PEG-14M (Polyox WSRN-3000) | 0.49 |
| Fragrance | 0.39 |
| Hydroxypropylcellulose (Klucel) | 0.02 |
| Dyes (e.g., FD&C Blue #1 and D&C Yellow #10) | Q.S. |
| Isopentane/Isobutane 85/15 Blend | 2.60 |
| | 100.00% |

The palmitic acid was melted at 75°–80° C. The hydroxypropylcellulose and propylene glycol isostearate were mixed to obtain Mixture 1 which was added to the melted palmitic acid. Using an eductor[1], the Polyox WSRN-3000 was dissolved in substantially all the water to obtain Solution 1. Solution 1 was then warmed to 75°–80° C. and maintained at this temperature. The sorbitol and dyes were then added to Solution 1 to form Solution 2. Solution 2 was then added to Mixture 1 to obtain Mixture 2. The 50:50 solution of triethanolamine and water was added to Mixture 2 at 75°–80° C. to obtain Mixture 3. Mixture 3 was then cooled to 50° C. and the fragrance was added to obtain Mixture 4. Mixture 4 was then cooled to 2° to 8° C and an 85:15 blend of isopentane/isobutane at a 2.60% level was introduced into Mixture 4. This intermediate was introduced into a container and the container was pressurized with approximately 10 grams of a hydrocarbon propellant. The pressure of the container was approximately 50±5 psig at 21° C.

[1]Available from Fox Valve Development Corporation Dover, N.J.

We claim:

1. A cleansing or cosmetic composition in the form of a stable, post-foaming gel consisting essentially of from about 40 to about 90 percent by weight water, from about 4 to about 25 percent by weight of a water-soluble soap; from about 0.5 to about 12 percent by weight aliphatic liquid post-foaming agent selected from the group consisting of saturated aliphatic hydrocarbons; from about 0.01 to about 0.02 percent by weight of at least one high viscosity water-soluble gelling agent, said high viscosity gelling agent selected from the group consisting of water-soluble hydroxyalkyl cellulose derivatives, water-soluble sucrose derivatives and water-soluble glucose derivatives, and from at least about 0.5 to about 2 percent by weight of a gel stabilizer selected from the group consisting of poly (ethylene oxides) having an average molecular weight of at least about $2 \times 10^5$; said gel stabilizer reducing the amount of said gelling agent and acting in conjunction with said gelling agent to form in said composition a high viscosity gel having a yield value sufficiently high to restrain said composition from foaming for at least about 60 seconds by preventing volatilization of the post-foaming agent thereby stabilizing said gel.

2. A composition according to claim 1 wherein the polyethylene oxide has a molecular weight of $4 \times 10^5$.

3. A composition according to claim 1 wherein the polyethylene oxide has a molecular weight of from about $3 \times 10^5$ to about $6 \times 10^5$ and the proportion is from about 0.3 to about 0.8 percent.

4. A composition according to claim 1 wherein the amount of said water in the composition is about 50 to about 80% by weight.

5. A composition according to claim 1 containing about 1 to about 4% by weight of said post-foaming agent.

6. A composition according to claim 1 wherein said post-foaming agent is a liquid that has a vapor pressure of about atmospheric (14.7 psia) at a temperature of about 40° C.

7. A composition according to claim 1 wherein said soap is present at from about 8 to about 15% by weight.

8. A composition according to claim 1 with a propellant dispersed continuously throughout the gel.

9. An aerosol container comprising the composition of claim 1 together with a propellant.

10. A foam composition comprising a composition of claim 1.

11. A cleansing or cosmetic formulation in the form of a stable post-foaming gel comprising from about 70 to about 80% by weight water, about 8 to about 10% of a $C_{12}$ to $C_{18}$ fatty acid, from about 5 to about 6% by weight triethanolamine, from about 1 to about 2% by weight propylene glycol isostearate, from about 1 to about 2% by weight of an aqueous solution of sorbitol that is at least 45 percent by weight sorbitol, from about 0.3% to about 0.8% by weight of poly(ethylene oxide) having a molecular weight of from about $3 \times 10^5$ to about $6 \times 10^5$, 0 to about 1% by weight of fragrance from about 0.02 to about 0.03% by weight of hydroxypropylcellulose, and about 2 to about 3% by weight of a liquid hydrocarbon having a vapor pressure of about 14.7 psia at 40° C.

12. A composition according to claim 1 containing an appropriate amount of a compatible dye.

* * * * *